United States Patent [19]
Auguste et al.

[11] Patent Number: 6,083,900
[45] Date of Patent: Jul. 4, 2000

[54] USE OF AN ORGANOPOLYSILOXANE FOR THE FIXING AND/OR SUSTAINED RELEASE OF PERFUME

[75] Inventors: Frederic Auguste, Chevilly-Larue; Isabelle Bara, Paris, both of France

[73] Assignee: L'Oreal, Paris, France

[21] Appl. No.: 09/015,270

[22] Filed: Jan. 29, 1998

[30] Foreign Application Priority Data

Jan. 31, 1997 [FR] France .................. 97 01105

[51] Int. Cl.[7] .............. A61K 7/46; A61K 7/06; A61K 7/11; A61K 31/74
[52] U.S. Cl. ................. 512/2; 512/4; 424/70.1; 424/70.11; 424/78.02; 424/78.03; 424/76.4; 424/70.12; 514/63
[58] Field of Search ............ 512/2, 4; 24/70.1, 24/70.11, 78.02, 78.03, 76.4, 70.12; 514/63

[56] References Cited

U.S. PATENT DOCUMENTS

| | | | |
|---|---|---|---|
| 4,374,236 | 2/1983 | Znaiden . | |
| 5,061,481 | 10/1991 | Suzuki et al. | 424/63 |
| 5,219,560 | 6/1993 | Suzuki et al. | 424/63 |
| 5,266,321 | 11/1993 | Shukuzaki et al. | 424/401 |
| 5,599,533 | 2/1997 | Stepniewski et al. | 424/78.02 |
| 5,654,362 | 8/1997 | Schulz, Jr. et al. | 524/862 |
| 5,738,841 | 4/1998 | Mellul et al. | 424/59 |
| 5,747,016 | 5/1998 | Yui et al. | 424/70.122 |
| 5,763,497 | 6/1998 | Ikeda et al. | 424/69 |
| 5,783,601 | 7/1998 | Tanahashi et al. | 514/557 |
| 5,811,487 | 9/1998 | Schulz, Jr. et al. | 524/862 |
| 5,827,509 | 10/1998 | Richard et al. | 424/60 |
| 5,849,314 | 12/1998 | Dobowski t al. | 424/401 |

FOREIGN PATENT DOCUMENTS

| | | |
|---|---|---|
| 0118625 | 9/1984 | European Pat. Off. . |
| 0295886 | 12/1988 | European Pat. Off. . |
| 0790055 | 8/1997 | European Pat. Off. . |
| 61-013961 | 1/1986 | Japan . |
| 02172906 | 7/1990 | Japan . |
| 07267819 | 10/1995 | Japan . |
| 09263525 | 10/1997 | Japan . |
| 10036228 | 2/1998 | Japan . |
| WO 9010436 | 9/1990 | WIPO . |

*Primary Examiner*—Gabrielle Brouillette
*Assistant Examiner*—Monique T. Cole
*Attorney, Agent, or Firm*—Oblon, Spivak, McClelland, Maier & Neustadt, P.C.

[57] ABSTRACT

The present invention relates to the use of at least one partially crosslinked, solid, elastomeric organopolysiloxane associated with a fatty phase, in a composition containing a perfume, for the fixing and/or sustained release of this perfume. The composition may be a cosmetic and/or dermatological composition and can be, in particular, in the form of a gel. The invention also relates to a cosmetic process to perfume, care for and/or cleanse the skin and/or the hair, by applying to the skin and/or the hair a composition containing, in a physiologically acceptable medium, a perfume and a partially crosslinked, solid, elastomeric organopolysiloxane associated with a fatty phase.

20 Claims, No Drawings

USE OF AN ORGANOPOLYSILOXANE FOR THE FIXING AND/OR SUSTAINED RELEASE OF PERFUME

BACKGROUND OF THE INVENTION

1. Field of the Invention

The present invention relates to the use of at least one partially crosslinked, solid, elastomeric organopolysiloxane associated with a fatty phase, in a composition for the fixing and/or sustained release of a perfume. The invention also relates to a process for treating the skin, both facial skin and body skin, and/or the hair, by application of this composition. This composition may be either a cosmetic composition or a dermatological composition.

2. Description of the Background

It is known that perfumes are a combination of different odorous substances which evaporate at different periods in time. Each perfume has what is known as a "head note", which is the odor that diffuses first when the perfume is applied or when the container holding it is opened, a "center or body note" which corresponds to the complete perfume (emitted for a few hours after the "head note") and a "base note" which is the most persistent odor (emitted for several hours after the "body note").

From time immemorial, humans have sought to perfume themselves and to perfume the objects which surround them or the locations in which they find themselves, this being both to mask strong and/or unpleasant odors and to give a good odor.

It is common to incorporate perfume into a certain number of products or compositions, in particular cosmetic and dermatological compositions. However, depending on the nature of these products or compositions, it is not always easy to incorporate a given perfume and/or to retain the desired olfactory effects. Several solutions have already been proposed to overcome these drawbacks.

For example, a solid soap containing a perfume which is released gradually in the course of the various uses of the soap is known from document JP-A-01,101,399. This perfumed soap is obtained by incorporating, firstly, the perfume with an organic composite mineral clay and then by mixing the perfumed clay with the soap composition. Unfortunately, the use of a clay for holding the perfume in this soap promotes the degradation of the perfume on contact with heat or with alkaline agent present in the composition.

Moreover, it is known to use cyclodextrins, which are cyclic molecules, to complex perfumes and thus allow their controlled release. Such compositions are described, for example, in documents EP-A-13,688 and U.S. Pat. No. 5,238,915. Unfortunately, the processes for including perfumes in cyclodextrins are complex. In addition, cyclodextrins may have a poor cosmetic feel.

Thus, the need remains for a perfumed composition, in particular a cosmetic and/or dermatological composition, which does not have the above drawbacks and which, in particular, can readily be prepared, thereby making it possible to increase the remanence of the perfume without the latter degrading, in particular on contact with the other constituents of the composition.

SUMMARY OF THE INVENTION

The inventors have discovered, surprisingly, that introducing a partially crosslinked, solid, elastomeric organopolysiloxane into a perfume composition prevents the perfume from degrading and allows it to persist for several hours on the person or object being perfumed.

Thus, the present invention provides a method of fixing and/or sustaining the release of a perfume from a composition by incorporating an effective amount of at least partially crosslinked, solid, elastomeric organopolysiloxane into a composition comprising a fatty phase and at least one perfume.

A more complete appreciation of the invention and many of the attendant advantages thereof will be readily obtained as the same becomes better understood by reference to the following detailed description.

DETAILED DESCRIPTION OF THE INVENTION

The term "elastomeric" as used herein refers to a supple, deformable material having viscoelastic properties and, in particular, the consistency of a sponge or a supple sphere.

It is known from EP-A-118,625 to use hexamethylcyclotrisiloxane, which is a volatile silicone oil, as a support for odorous substances for ambient-air deodorizers. However, the purpose atmosphere on account of the volatility of this oil, rather than to fix the perfume in the composition containing it.

However, the organopolysiloxane of the present invention is not a volatile compound and it allows, in contrast, sustained release of the perfume over time when it is applied.

The elastomeric organopolysiloxanes in accordance with the invention may be partially or totally crosslinked. When included in a fatty phase, they become converted, depending on the amount of fatty phase used, from a product of spongy appearance when they are used in the presence of low amounts of fatty phase, into a homogeneous gel in the presence of larger amounts of fatty phase. The gelation of the fatty phase by these elastomers may be total or partial.

The elastomers of the invention can be conveyed in the form of a gel consisting of an elastomeric organopolysiloxane, including at least one hydrocarbon oil and/or a silicone oil. Also, the fatty phase associated with the elastomeric organopolysiloxane may consist of one or more of these oils.

The elastomeric organopolysiloxanes used in the present invention may be selected from the crosslinked polymers described in patent application EP-A-0,295,886, incorporated herein by reference. According to this application, they are obtained by an addition and crosslinking reaction, in the presence of a platinum-type catalyst, of at least:

(a) one organopolysiloxane having at least two lower alkenyl groups per molecule, these alkenyl groups containing two to six carbon atoms, and (b) one organopolysiloxane having at least two hydrogen atoms linked to a silicon atom per molecule.

The elastomeric organopolysiloxanes for the present invention may also be selected from those described in patent U.S. Pat. No. 5,266,321 from column 3, line 41 to column 7, line 2, incorporated herein by reference. According to this patent, they are chosen, in particular, from:

(i) organopolysiloxanes comprising units $R_2SiO$ and $RSiO_{1.5}$ and optionally units $R_3SiO_{0.5}$ and/or $SiO_2$ in which the radicals R, independently of each other, denote a hydrogen, an alkyl such as methyl, ethyl or propyl, an aryl such as phenyl or tolyl, an unsaturated aliphatic group such as vinyl, and in which the weight ratio of the units $R_2SiO$ to the units $RSiO_{1.5}$ ranges from 1/1 to 30/1; and (ii) organopolysiloxanes which are insoluble and swellable in silicone oil, obtained by addition of an organohydrogenopolysiloxane (1) and of an organopolysiloxane (2) having unsaturated aliphatic groups, such that the amount of hydrogen or of unsaturated aliphatic groups in (1) and (2) respectively is between 1 and 20 mol % when the organopolysiloxane is non-cyclic and between 1 and 50 mol % when the organopolysiloxane is cyclic.

The organopolysiloxanes in the composition of the invention are, for example, those sold under the names KSG6 from Shin-Etsu, Trefil E-505C or Trefil E-506C from Dow Corning, Gransil (SR-CYC, SR DMF10, SR-DC556) from Grant Industries, or those sold in the form of preconstituted gels: KSG15, KSG17, KSG16, KSG18, KSG26A, and KSG26B from Shin-Etsu, Gransil SR 5CYC gel, Gransil SR DMF 10 gel and Gransil SR DC556 gel, and 1229-02-167 and 1229-02-168 from General Electric. A mixture of these commercial products may also be used.

The elastomeric organopolysiloxanes used according to the invention do not dry out the skin and provide good cosmetic properties. They lead to compositions that feel comfortable when applied, soft and non-sticky to the touch. This softness is due in particular to the texture of the organopolysiloxanes. In addition, they make it possible to fix the perfume and to obtain very good remanence of the composition obtained, in particular when this composition is in the form of a gel.

The fatty phase associated with the elastomeric organopolysiloxane preferably comprises one or more hydrocarbon and/or silicone and/or fluoro oils. These oils can consist of the perfume extract itself; in this case, the perfume comprises fatty substances. The oils in the fatty phase can be volatile or non-volatile and are chosen depending on their solubility parameters and their chemical structure. The oil used or the mixture of oils used preferably has average Hansen solubility parameters dD, dP and dH at 25° C. which satisfy the following three conditions:

(1) $dD \leq 20$ $(J/cm^3)^{1/2}$ (2) $dP \leq 10$ $(J/cm^3)^{1/2}$ (3) $dH \leq 15$ $(J/cm^3)^{1/2}$.

The definition of solvents in the three-dimensional solubility space according to Hansen is described in the article by C. M. Hansen: "The three-dimensional solubility parameters" J. Paint Technol. 39, 105 (1967), incorporated herein by reference. This space is defined by the parameters dD, dP, dH; they are expressed in $(J/cm^3)^{1/2}$:

dD characterizes the London dispersion forces derived from the formation of dipoles induced during molecular impacts;

dP characterizes the Debye interaction forces between permanent dipoles and the Keesom interaction forces between induced dipoles and permanent dipoles;

dH characterizes the specific forces of interaction (of the hydrogen bonding, acid/base, donor/acceptor, for example).

The hydrocarbon oils can be chosen from oils of animal origin, oils of plant origin, synthetic oils such as hydrogenated isoparaffin, synthetic esters and ethers, and mixtures thereof.

The silicone oils can be chosen from linear polysiloxanes which are liquid or pasty at room temperature, such as alkylpolysiloxanes, alkylphenylpolysiloxanes, alkylpolydimethylsiloxanes and cyclic polysiloxanes such as octamethylcyclopentasiloxane and decamethylcyclopentasiloxane, or mixtures thereof.

The silicone oils can also be chosen from oils which are suitable as co-solvents for the elastomeric organopolysiloxane and for the perfume.

These oils which are suitable as co-solvents are, for example, volatile silicones containing a linear silicone structure and units containing a pendant alkyl chain and/or an alkyl chain at the end of the silicone structure, these alkyl chains being linear or branched and containing 3 to 10 carbon atoms. The volatile silicones containing an alkyl chain preferably have the formula (1) below;

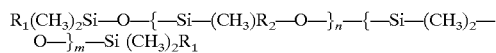

where $R_1$ and $R_2$ are each, independently, H, methyl or a linear, or branched alkyl chain having from 3 to 10 carbon atoms, n and m are each, independently, integers ranging from 0 to 10, provided that when $R_1$ is H or methyl, then n is other than 0 and $R_2$ represents an alkyl chain having, 3 to 10 atoms.

Advantageously, the volatile silicones of formula (1) have a molecular weight ranging from 290 to 3000 and a volatility or decree of evaporation Nv generally of between 150 and 500 seconds (time corresponding to the evaporation of 0.2 ml of volatile silicone at 23° C. in a stable atmosphere at 50% relative humidity).

As volatile silicones containing an alkyl chain which can be used in the invention, mention may be made of alkylheptamethyltrisiloxanes with an alkyl group containing from 4 to 8 carbon atoms, such as, for example, hexylheptamethyltrisiloxane of formula: $(CH_3)_3$—Si—O—Si$(CH_3)$ $(C_6H_{13})$—O—Si$(CH_3)$ $_3$; octylheptamethyltrisiloxane of formula: $(CH_3)_3$—Si—O—Si$(CH_3)$ $(C_8H_{15})$—O—Si $(CH_3)$ $_3$; and mixtures thereof.

Preferably, the oil used as co-solvent is hexylheptamethyltrisiloxane.

The co-solvent is, in particular, present in order to obtain a composition in gel form.

The perfume may comprise any perfume or mixture of perfumes of natural or synthetic origin, including essential oils. The perfume can be present in the composition in an amount ranging from 0.001 to 50% and preferably from 0.1 to 30% of the total weight of the composition. The fatty phase is present in an amount ranging from 0.1 to 80%. These ranges for the perfume and fatty phase in the composition include all specific values and subranges therebetween.

The elastomeric organopolysiloxane(s) used according to the invention is (are) preferably present at an active material concentration ranging from 0.1 to 50% of the total weight of the composition, including all specific values and subranges therebetween. However, these proportions of organopolysiloxane, and those of the fatty phase, can vary according to the pharmaceutical form which it is desired to obtain.

The composition according to the invention is preferably in gel form and comprises, relative to the total weight of the composition, 0.001 to 50%, and better still 0.01 to 50%, of perfume, 1 to 50%, and better still 20 to 50%, of organopolysiloxane and 10 to 80%, and better still, 20 to 70%, of fatty phase. The ranges noted above include all specific values and subranges therebetween.

The composition according to the invention may be especially suitable for topical use and can constitute in particular a cosmetic and/or dermatological composition. In this case, it contains a physiologically acceptable medium. The term "physiologically acceptable" is understood to refer to a medium which is compatible with human skin, eyes and keratin fibers.

As indicated above, the composition of the invention is preferably in the form of a gel. In a known manner, the composition of the invention may also contain the usual adjuvants in the cosmetic and dermatological fields, such as fatty substances, hydrophilic or lipophilic active agents, preserving agents, screening agents, pigments (for example pearlescent agents) and dyestuffs. The amounts of these various adjuvants are those used conventionally in the fields considered, and, for example, from 0.01 to 20% of the total weight of the composition (including all specific values and subranges therebetween). Needless to say, these adjuvants must be of a nature and used in an amount such that they do not disrupt the composition of the invention.

As fatty substances which can be used in the invention, mention may be made, in addition to the oils indicated above, of waxes, in particular hydrocarbon waxes or silicone waxes.

The composition can be used in particular as a product to cleanse, care for and/or perfume the skin and/or the hair, and/or as a make-up product, while at the same time ensuring perfuming of the skin and/or the hair. The composition can also be used solely as a perfumery product.

While the compositions of the present invention may contain the various adjuvants noted above, one embodiment may exclude cosmetic powder materials as defined by U.S. Pat. No. 5,266,321, column 7, lines 32–45, incorporated herein by reference. Another embodiment may exclude an acrylic water-soluble polymer containing glycerine as defined in U.S. Pat. No. 5,266,3 2 1, column 7, lines 46–65, incorporated herein by reference. Yet another embodiment may exclude the cosmetic powder materials and the acrylic water-soluble polymer containing glycerine.

Thus, the present invention also relates to a cosmetic process to perfume and/or cleanse and/or care for the skin and/or the hair, this process consisting, in applying to the skin and/or the hair a composition comprising, in a physiologically acceptable medium, at least one at least partially crosslinked, solid, elastomeric organopolysiloxane associated with a fatty phase, containing at least one perfume.

Having generally described this invention, a further understanding can be obtained by reference to certain specific examples which are provided herein for purposes of illustration only and are not intended to be limiting unless otherwise specified.

EXAMPLES

| Example 1: Perfumed gel | |
|---|---|
| 1. Crosslinked organopolysiloxane, at 60% in non-volatile PDMS (KSG6) | 35% |
| 2. Perfume | 10% |
| 3. Hexylheptamethyltrisiloxane (DC2-1731 Volatile Fluid sold by Dow Corning) | 55% |

The amounts are given as a percentage by weight. A perfumed gel which is soft on application, having a high level of remanence over time, is obtained.

French Patent Application 97-01105, filed Jan. 31, 1997, is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method comprising incorporating an effective amount for fixing and/or sustaining the release of perfume of at least one at least partially crosslinked, solid, elastomeric organopolysiloxane into a, non-cosmetic powder-containing composition consisting essentially of a fatty phase and at least one perfume, wherein the fatty phase contains at least one oil which is suitable as a co-solvent for the perfume and for the elastomeric organopolysiloxane, wherein said oil is represented by the formula:

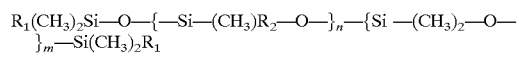

wherein
   $R_1$ and $R_2$ are each independently, H, methyl, or a linear or branched alkyl chain having from 3 to 10 carbon atoms,
   n and m are each, independently, an integer from 0 to 10,
   provided that when $R_1$ is H or methyl, then n is other than 0 and $R_2$ represents an alkyl chain 3 to 10 atoms.

2. The method of claim 1, wherein the composition is in the form of a gel.

3. The method of claim 1, wherein the organopolysiloxane is obtained by an addition and crosslinking reaction, in the presence of a catalyst, of at least:
   (a) one organopolysiloxane having at least two lower alkenyl groups per molecule, and
   (b) one organopolysiloxane having at least two hydrogen atoms linked to a silicon atom per molecule.

4. The method of claim 1, wherein the organopolysiloxane is selected from the group consisting of
   (i) organopolysiloxanes comprising units $R_2SiO$ and $RSiO_{1.5}$ and optionally units $R_3SiO_{0.5}$ and/or $SiO_2$ in which the radicals R, independently of each other, denote a hydrogen, an alkyl, an aryl, an unsaturated aliphatic group and in which the weight ratio of the units $R_2SiO$ to the units $RSiO_{1.5}$ ranges from 1/1 to 30/1, and
   (ii) organopolysiloxanes which are insoluble in silicone oil, obtained by addition of an organohydrogenopolysiloxane (1) and of an organopolysiloxane (2) having unsaturated aliphatic groups, such that the amount of hydrogen or of unsaturated aliphatic groups in (1) and (2) respectively is between 1 and 20 mol % when the organopolysiloxane is non-cyclic and between 1 and 50 mol % when the organopolysiloxane is cyclic.

5. The method of claim 1, wherein the composition comprises 0.1 to 50% by weight of the organopolysiloxane.

6. The method of claim 1, wherein the fatty phase additionally comprises at least one oil selected from the group consisting of hydrocarbon oils, silicone oils, fluoro oils, and mixtures thereof.

7. The method of claim 6, wherein the hydrocarbon oils comprise oils of animal origin, oils of plant origin, synthetic oils, or mixtures thereof.

8. The method of claim 6, wherein the silicone oils are selected from the group consisting of linear polysiloxanes which are liquid or pasty at room temperature, cyclic polysiloxanes, and mixtures thereof.

9. The method of claim 1, wherein the co-solvent is comprises hexylheptamethyltrisiloxane, octylheptamethyltrisiloxane, or a mixture thereof.

10. The method of claim 1, wherein the composition comprises from 0.001 to 50% by weight of the perfume.

11. The method of claim 1, wherein the composition comprises from 0.1 to 80% by weight of the fatty phase.

12. The method of claim 1, wherein the composition comprises 0.001 to 50% by weight of the perfume, 1 to 50% by weight of the organopolysiloxane, and 10 to 80% by weight of the fatty phase.

13. The method of claim 12, wherein the composition comprises 0.01 to 50% by weight of the perfume, 20 to 50% by weight of the organopolysiloxane, and 20 to 70% by weight of the fatty phase.

14. The method of claim 1, wherein the composition is suitable as a cosmetic and/or dermatological composition.

15. The method of claim 1, wherein the composition is suitable for cleansing and/or caring for the skin.

16. The method of claim 1, wherein the composition is suitable for perfuming the skin.

17. A non-cosmetic powder-containing perfume composition consisting essentially of:

0.001 to 50% by weight of at least one perfume, 10 to 80% by weight of a fatty phase which contains at least one oil which is suitable as a co-solvent for the perfume and for an elastomeric organopolysiloxane, wherein said oil is represented by the formula:

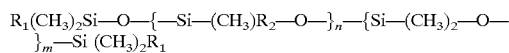

wherein $R_1$ and $R_2$ are each, independently, H, methyl, or a linear or branched alkyl chain having from 3 to 10 carbon atoms, n and m are each, independently, an integer from 0 to 10, provided that when $R_1$ is H or methyl, then n is other than 0 and $R_2$ represents an alkyl chain having 3 to 10 atoms, and 1% to 50% by weight of at least one partially crosslinked, solid, elastomeric organopolysiloxane selected from the group consisting of (i) organopolysiloxanes comprising units $R_2SiO$ and $RSiO_{1.5}$ and optionally units $R_3SiO_{0.5}$ and/or $SiO_2$ in which the radicals R, independently of each other, denote a hydrogen, an alkyl, an aryl, an unsaturated aliphatic group and in which the weight ratio of the units $R_2SiO$ to the units $RSiO_{1.5}$ ranges from 1/1 to 30/1, and (ii) organopolysiloxanes which are insoluble in silicone oil, obtained by addition of an organohydrogenpolysiloxane (1) and of an oganopolysiloxane (2) having unsaturated aliphatic groups, such that the amount of hydrogen or of unsaturated aliphatic groups in (1) and (2) respectively is between 1 and 20 mol % when the organopolysiloxane is non-cyclic and between 1 and 50 mol % when the organosiloxane is cyclic.

18. The perfume composition of claim 17, which is in the form of a gel.

19. A method of perfuming and/or cleansing and/or caring for the skin and/or the hair, comprising applying to the skin and/or the hair a, non-cosmetic powder-containing perfume composition consisting essentially of:

0.001 to 50% by weight of at least one perfume, 10 to 80% by weight of a fatty phase which contains at least one oil which is suitable as a co-solvent for the perfume and for an elastomeric organopolysiloxane, wherein said oil is represented by the formula:

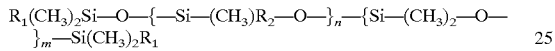

wherein $R_1$ and $R_2$ are each, independently, H, methyl, or a linear or branched alkyl chain having from 3 to 10 carbon atoms, n and m are each, independently, an integer from 0 to 10, provided that when $R_1$ is H or methyl, then n is other than 0 and $R_2$ represents an alkyl chain having 3 to 10 atoms, and 1% to 50% by weight of at least one partially crosslinked, solid, elastomeric organopolysiloxane selected from the group consisting of (i) organopolysiloxanes comprising units $R_2SiO$ and $RSiO_{1.5}$ and optionally units $R_3SiO_{0.5}$ and/or $SiO_2$ in which the radicals R, independently of each other, denote a hydrogen, an alkyl, an aryl, an unsaturated aliphatic group and in which the weight ratio of the units $R_2SiO$ to the units $RSiO_{1.5}$ ranges from 1/1 to 30/1, and (ii) organopolysiloxanes which are insoluble in silicone oil, obtained by addition of an organohydrogenpolysiloxane (1) and of an oganopolysiloxane (2) having unsaturated aliphatic groups, such that the amount of hydrogen or of unsaturated aliphatic groups in (1) and (2) respectively is between 1 and 20 mol % when the organopolysiloxane is non-cyclic and between 1 and 50 mol % when the organosiloxane is cyclic.

20. The perfume composition of claim 17, consisting of 35% of said elastomeric organopolysiloxane, 10% of said perfume, and 55% of hexylheptamethyl trisiloxane as said fatty phase.

* * * * *